United States Patent [19]
Veber et al.

[11] 3,948,971
[45] Apr. 6, 1976

[54] N-PROTECTED-α-AMINO ACID COMPOUNDS

[75] Inventors: Daniel F. Veber, Ambler; Stephen F. Brady, Meadowbrook, both of Pa.

[73] Assignee: Merck & Co., Inc., Rahway, N.J.

[22] Filed: May 3, 1972

[21] Appl. No.: 249,976

[52] U.S. Cl.. 260/471 C; 260/112.5 R; 260/293.65; 260/293.7; 260/293.71; 260/293.74; 260/309; 260/326.2; 260/326.42; 260/481 C; 260/482 C
[51] Int. Cl.² ................................. C07C 125/06
[58] Field of Search .................... 260/471 C, 482 C

[56] References Cited
UNITED STATES PATENTS
3,839,395   10/1974   Otsuka et al. ............... 260/482 C X
3,896,152   7/1975    Otsuka et al. ............... 260/471 C X OTHER PUBLICATIONS
Finak; I. L., Organic Chemistry, Vol. I, (1963), Pub. by Richard Clay & Co., Ltd., Great Britain; p. 382 relied on.

Otsuka et al., Chemical Abstracts, Vol. 78 (1973) 124,891w.

Primary Examiner—Richard L. Raymond
Attorney, Agent, or Firm—Henry H. Bassford, Jr.; J. Jerome Behan

[57] ABSTRACT

Novel N-protected-α-amino acid compounds are disclosed in which the amino functionality is protected by a 1-methylcyclobutyloxycarbonyl or 1-methylcyclohexyloxycarbonyl. Processes for the synthesis of amino acids containing these protecting groups and the use of these novel amino acid compounds in the preparation of peptides are also disclosed.

12 Claims, No Drawings

N-PROTECTED-α-AMINO ACID COMPOUNDS

The present invention relates to novel N-protected-α-amino acid compounds. More particularly, this invention relates to novel protected amino acid compounds in which the amino functionality is protected with 1-methylcyclobutyloxycarbonyl or 1-methylcyclohexyloxycarbonyl radicals and the use of these compounds in peptide synthesis.

A major object of present day research in peptide and protein chemistry is the development of new and superior methods of peptide synthesis. The fundamental peptide forming reaction involves coupling of two or more amino acids in a manner to form an amide linkage between the molecules. Since amino acids are at least bifunctional, it is necessary to render inactive all functionalities in a given amino acid which are not directly employed in the coupling reaction. Failure to block or protect the reactive functionalities will result in formulation of a large amount of undesirable by-products which will lower yields and make purification more difficult. There are several well known methods for rendering inactive the amino functionality of amino acids with protecting groups in such a manner that only the carboxy functionality is available to react in forming the amide linkage. It is necessary for the protecting group to be readily attached to the amino acid before amide formation, to be stable to the reaction conditions employed in formation and purification of the peptide and to be readily removed from the resulting peptide, after coupling, without simultaneous rupture of the newly formed peptide linkage. These requirements are met by the 1-methylcyclobutyloxycarbonyl and 1-methylcyclohexyloxycarbonyl groups of this invention. The N-protected-α-amino acid compounds of this invention and the methods of peptide synthesis employing these compounds represent an advance in peptide synthesis by improving yields and eliminating by-product formation.

One of the most commonly employed protecting groups for the amino functionality of α-amino acids in peptide synthesis is the tert-butyloxycarbonyl (t-Boc) blocking group. This blocking group has found wide use in peptide chemistry because it is readily attached to the amino functionality of amino acids and the cleavage of the t-Boc group occurs upon relatively short action of acids. In spite of the wide applicability of the t-Boc group, certain problems have arisen associated with the use of this blocking group in peptide synthesis. One problem is concerned with the partial loss of t-Boc during isolation procedures using 50% aqueous acetic acid, a solvent employed in purification of peptides by gel filtration. It has been found that the 1-methylcyclobutyloxycarbonyl blocking group is more stable than the t-Boc group in 50% aqueous acetic acid and yet it is sufficiently labile under acidic conditions to be useful in peptide synthesis. The advantage of the 1-methylcyclobutyloxycarbonyl protecting group is that it facilitates manipulation of protected peptides over a longer period of time under conditions where loss of t-Boc has been observed.

In synthesizing large peptides, it is common to employ both the tert-butyloxycarbonyl (t-Boc) and the carbobenzoxycarbonyl (Cbz) as blocking groups for the amino functionality of various amino acid residues in the peptide chain. Attempts to selectively remove the t-Boc group in the presence of the Cbz group under acid conditions, for examples trifluoroacetic acid, anhydrous hydrofluoric acid, anhydrous hydrogen chloride in ethyl acetate, results in partial loss of the Cbz group along with cleavage of the t-Boc group. The 1-methylcyclohexyloxycarbonyl blocking group has been found to be more labile than the t-Boc protecting group under acid conditions, and as a result, the 1-methylcyclohexyloxycarbonyl group is useful in situations involving its removal in the presence of the Cbz protecting group elsewhere in the molecule.

The novel blocking groups of the present invention, namely 1-methylcyclobutyloxycarbonyl and 1-methylcyclohexyloxycarbonyl, can be employed in all cases where the t-Boc protecting group is employed in the synthesis of peptides.

The novel N-protected-α-amino acids of this invention may be illustrated by the following formula:

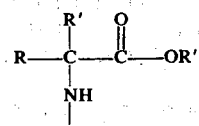

wherein X is a monovalent protective radical selected from the group consisting of 1-methylcyclobutyloxycarbonyl and 1-methylcyclohexyloxycarbonyl, R and R' represent the residue remaining of an α-amino acid, and R'' represents hydrogen, loweralkyl radical straight or branched chain having from 1-6 carbon atoms, for example, methyl, ethyl, n-propyl, isopropyl, butyl, t-butyl, aralkyl for example benzyl, phenylethyl, aryl, for example phenyl, p-nitrophenyl, heterocyclic radical, for example N-succinimide, N-piperidyl, and the like.

The starting materials in preparing the novel N-protected amino compounds of the present invention are the naturally occurring α-amino acids and include the following: glycine, alanine, valine, leucine, isoleucine, phenylalanine, tyrosine, proline, hydroxyproline, serine, threonine, cysteine, cystine, methionine, aspartic acid, glutamic acid, arginine, lysine, ornithine, histidine, and the like.

The novel N-protected-α-amino acid compounds of this invention are conveniently prepared by reacting 1-methylcyclobutylchloroformate of 1-methylcyclohexylchloroformate with an appropriate α-amino acid or ester thereof.

Formation of the chloroformate compounds can be accomplished by reacting the starting alcohol, 1-methylcyclobutanol or 1-methylcyclohexanol with phosgene in an organic solvent. The reaction is run by adding a solution of the alcohol in an organic solvent such as benzene, ether, methylene chloride, and the like to a solution of phosgene in the same solvent. An excess of phosgene, generally from 2-5 moles of phosgene per mole of alcohol is employed in preparing the chloroformate compounds. The alcohol solution is added slowly to the phosgene solution at low temperatures of from −30°C. to +25°C. and preferably about 0°C. The reaction proceeds to completion by stirring at 0°C. Formation of the chloroformate compound is accompanied by the generation of hydrogen chloride and an acid acceptor, for example an organic amine compound can be employed to remove the gas from the reaction medium by precipitating out as the hydrochloride salt. Organic amines which are useful in this step of the reaction include pyridine, triethylamine, N-methylmorpholine, and the like. The amine hydrochloride salt is removed from the reaction mixture by filtration and the excess phosgene is removed by evacuating under aspirator pressure. Removal of the solvent in vacuo affords the 1-methylcyclobutylchloroformate or the corresponding 1-methylcyclohexylchloroformate. The chloroformate compounds tend to be unstable and should be employed immediately or maintained at a temperature of about 0°C. Due to the instability of the chloroformate compounds, it is preferable to employ these compounds as a solution in the solvent in which it was prepared.

Formation of the N-protected amino acid compounds of this invention is carried out by treating approximately equimolar quantities of the chloroformate reagent and an α-amino acid or ester thereof in an appropriate solvent at reduced temperatures in a basic medium for a period of time ranging from several minutes to several hours for the reaction to proceed to substantial completion as determined by thin layer chromatography.

The reaction of the α-amino acid with the chloroformate reagent is carried out in a basic aqueous solution. The reaction of an α-amino acid ester, such as a lower-alkyl ester, for example, the methyl, ethyl, n-propyl, isopropyl, t-butyl esters and the like is carried out in an organic solvent. Appropriate solvents are for example chloroform, tetrahydrofuran, dimethylformamide, acetonitrile, isopropanol, and the like. Preferably, the chloroformate is added portion-wise to the amino acid dissolved or suspended in the organic solvent. The reaction is run in a basic medium generally at a pH of from 7 to 13, and preferably pH 9. A base, for example sodium hydride or an organic amine such as triethylamine, N-methylmorpholine, or diisopropylethylamine, is added to the amino acid to adjust the pH to 9. During the addition of the chloroformate component, base is added to maintain the pH within the required range. In general, the temperature at which the reaction is carried out ranges from about 0°C. to 25°C. Addition of the chloroformate compound is preferably conducted at about 0°C. and the reaction is then allowed to proceed to completion at ambient temperature. Upon completion of the reaction, the N-protected-α-amino acid product is separated by conventional means such as extraction. If the product is in the form of its lower-alkyl ester, saponification to the free acid is accomplished by treating an aqueous alcoholic solution with base, for example sodium hydroxide, and allowing the reaction to run to completion at room temperature. Acidification of the reaction mixture with mineral acid, for example sulfuric acid, hydrochloric acid, and removal of the solvent affords the N-protected-α-amino acid by methods known in the art.

The novel blocking groups of this invention can be removed from an amino acid or peptide containing said blocking group by treatment with acid. Cleavage of the 1-methylcyclobutyloxycarbonyl group and the 1-methylcyclohexyloxycarbonyl group can be carried out in the presence of anhydrous hydrofluoric acid, trifluoroacetic acid, formic acid, anhydrous hydrogen chloride in an organic solvent such as ethyl acetate, acetic acid, dioxane, and the like. The cleavage with anhydrous hydrofluoric acid is carried out by treating the blocked amino acid or peptide at −40°C. to +20°C. and preferably at 0°C. for 1 hour. The reaction with trifluoroacetic acid is carried out by treating the protected amino acid or peptide at 25°C. for 30 minutes. The total absence of the blocking group is determined by thin layer chromatography.

Another aspect of the present invention relates to "active esters" of novel N-protected-α-amino acid compounds of this invention and the use of these esters in the synthesis of peptides. According to this feature, a reactive ester, for example N-hydroxysuccinimide, 1-piperidyl, and p-nitrophenyl esters of N-protected-α-amino acids, are reacted with a derivative of an α-amino acid or derivative of a peptide to afford a higher peptide.

The novel esters of this invention may be prepared by reacting N-hydroxysuccinimide, 1-hydroxypiperidine, or p-nitrophenol with an N-protected-α-amino acid in a suitable solvent such as dioxane in the presence of N,N'-dicyclohexylcarbodiimide. The reaction is carried out by dissolving approximately equimolar quantities of N-hydroxysuccinimide, 1-hydroxypiperidine, or p-nitrophenol and N-protected-α-amino acid in an appropriate solvent preferably a non-aqueous solvent at room temperature or below, then dissolving approximately a 10% excess of an equimolar quantity of N,N'-dicyclohexylcarbodiimide in this solution while maintaining the reduced temperature, and then maintaining the resulting solution at reduced temperature for a period of time ranging from an hour to several days for the reaction to proceed to substantial completion. Appropriate solvents are, for example dioxane, tetrahydrofuran, dimethylformamide and the like. In general, the temperature at which the reaction is carried out ranges from about −10°C. to about 25°C. After the reaction has proceeded to substantial completion, any by-products such as N,N'-dicyclohexylurea may be separated from the desired ester product by conventional means, for example filtration.

The novel N-protected-α-amino acid compounds of this invention are useful in peptide synthesis. For preparing peptides according to the present invention, the condensation methods usual in peptide chemistry may be used, such as the carbodiimide or the azide methods, or, for example the mixed anhydrides or activated esters. The peptides are built up from amino acids by condensing members selected from the group consisting of naturally occurring α-amino acids, peptides built up from said amino acids, and derivatives thereof, and wherein at least one component of said members has the α-amino functionality protected with a 1-methylcyclobutyloxycarbonyl or 1-methylcyclohexyloxycarbonyl blocking group.

In preparing peptides with the novel N-protected-α-amino acid compounds of this invention, other functional groups of the amino acids, for example, —OH, —SH, —COOH, and other —NH$_2$ groups may or must be protected by methods generally employed in peptide chemistry (see E. Schroder and K. Lubke, The Peptides, Academic Press, Inc., New York and London, 1965, vol. I, pages 3–75). Amino groups can be protected by acyl-type protecting groups, for example formyl, acetyl, chloroacetyl, trichloroacetyl, trifluoroacetyl, benzoyl, phthalyl, phenacetyl blocking groups and the like; urethan protecting groups, such as carbobenzoxy, substituted carbobenzoxy, tert-butyloxycarbonyl, alkyltype protecting groups, such as trityl, benzyl, dibenzyl, and the like. Carboxyl groups can be protected by esters; alkyl esters, for example, methyl, ethyl, tert-butyl, benzyl and substituted benzyl groups. Sulfhydryl groups can be protected by trityl, benzhydryl, or acetamidomethyl groups. The hydroxyl groups can be protected by trityl, benzyl, or tert-butyl groups.

An example of the use of the novel N-protected-α-amino acid compounds of this invention in peptide synthesis is the preparation of α-aspartyl-phenylalanine methyl ester, a known sweetening agent. The dipeptide is conveniently prepared by coupling N-(1-methylcyclobutyloxycarbonyl) aspartic anhydride with phenylalanine methyl ester hydrochloride. Introduction of the N-(1-methylcyclobutyloxycarbonyl blocking group into aspartic acid is accomplished by reacting 1-methylcyclobutylchloroformate with aspartic acid dimethyl ester in accordance with the process of this invention. Equimolar quantities of the chloroformate and aspartic acid dimethyl ester are reacted in chloroform at 0°C. at pH 8. Reaction is carried out by portion-wise addition of 1-methylcyclobutyl chloroformate to the aspartic acid suspended in chloroform. Triethylamine is added to the reaction during the addition to maintain pH 8. After allowing the reaction to run to completion at room temperature, the reaction mixture is treated according to the procedure outlined above to afford the N-(1-methylcyclobutyloxycarbonyl) aspartic acid dimethyl ester. The free acid is obtained by saponifying the ester in a basic aqueous methanol solution. After acidifying the reaction mixture with sulfuric acid, the N-(1-methylcyclobutyloxycarbonyl) aspartic acid is isolated by extraction.

N-(1-methylcyclobutyloxycarbonyl) aspartic anhydride is prepared by treating the protected aspartic acid with dicyclohexylcarbodiimide in dioxane. After the reaction is completed, the dicyclohexyl urea is removed by filtration and evaporation of the solvent affords N-(1-methylcyclobutyloxycarbonyl) aspartic anhydride.

Coupling of N-(1-methylcyclobutyloxycarbonyl) aspartic anhydride with phenylalanine methyl ester hydrochloride is carried out in an organic solvent, for example dimethylformamide in the presence of an amine such as triethylamine. The reaction is stirred for several hours at a temperature of about 20°C. Upon completion of the coupling reaction the solvent is removed and the residue dissolved in ethyl acetate. Extraction with acid and removal of the solvent affords a mixture of α and β N-(1-methylcyclobutyloxycarbonyl) aspartyl-phenylalanine methyl ester. The blocking group is removed by stirring the protected dipeptide ester in anhydrous hydrofluoric acid at 0°C. The α-isomer of aspartyl-phenylalanine methyl ester is isolated by treating an aqueous mixture of the α- and β- isomers with β-phenylpropionic acid at a pH of from 3–5. The α-aspartyl phenylalanine methyl ester β-phenylpropionic adduct precipitates out of the solution. The resulting adduct is readily decomposed by treatment with acid to produce α-aspartyl phenylalanine methyl ester.

The following examples are given for purposes of illustration and should not be considered limitations of this invention, many apparent variations of which are possible without departing from the spirit or scope thereof. The α-amino acids used in the examples are in the L-configuration. The process is equally applicable to D-α-amino acids and to racemic mixtures.

EXAMPLE 1

N-(1-Methylcyclobutyloxycarbonyl)-Phenylalanine

A. Preparation of 1-Methylcyclobutyl Chloroformate

To 10 ml. of 1.5 molar solution methyl lithium in ether is added a solution of 1 gm. (14 mM) of cyclobutanone in 5 ml. of dry ether at 0°C. under nitrogen. The reaction is stirred three hours at 25°C. and quenched with saturated sodium chloride solution at 0°C. Water is added to dissolve the salts and the aqueous layer is extracted twice with ether; the ether extracts are combined and washed twice with saturated sodium chloride solution and then dried over sodium sulfate. The solvent is removed by distillation and any residual solvent is removed by evacuation at water pump pressure and a bath temperature of 15°C. 1.35 Gm. of 1-methylcyclobutanol is obtained. The infrared spectra of this compound indicates the absence of any carbonyl and strong hydroxyl absorption at 3.0 microns.

A solution of 0.55 gm. (6.5 mM) of 1-methylcyclobutanol, and 0.44 ml. of pyridine in 10 ml. of benzene is added to a solution of phosgene in 10 ml. of benzene at 0°C. over a 30 minute period. The reaction is allowed to stir for 30 minutes and then filtered to remove pyridine hydrochloride formed during the reaction. Excess phosgene is removed by evaporation at reduced pressure and the volume of the benzene solution is reduced to 4–5 ml; the benzene solution of 1-methylcyclobutylchloroformate is employed in the following reaction.

B. N-(1-Methylcyclobutyloxycarbonyl)-Phenylalanine

A suspension of 171 mg. (0.74 mM) of phenylalanine methyl ester hydrochloride in 10 ml. of chloroform is cooled to 0°C. and the pH adjusted to 8 by addition of triethylamine. 1-Methylcyclobutyl chloroformate 1.5 mM is added portion-wise at 0°C. and the pH of the reaction is maintained at 8 by addition of triethylamine. Upon completion of the addition, the reaction is stirred overnight at 20°–25°C. The reaction solution is washed successively with 10 ml. portions of a saturated sodium bicarbonate solution, 50% saturated solution of sodium chloride, 0.2 N sulfuric acid saturated with sodium sulfate, 50% saturated solution of sodium chloride (twice), and the chloroform solution is dried over sodium acetate. Removal of the chloroform affords N-(1-methylcyclobutyloxycarbonyl)-phenylalanine methyl ester. Saponification of the above ester is carried out by dissolving the residue in 10 ml. of methanol, water (10 ml.) is added and the pH is adjusted to 12 by addition of 2 N sodium hydroxide. After stirring overnight at 25°C., the pH is adjusted to 7 with 2 N sulfuric acid. The methanol is removed in vacuo and saturated sodium bicarbonate solution is added to the water solution. The aqueous bicarbonate solution is washed two times with ether and then the pH is adjusted to 3 by addition of concentrated hydrochloric acid. The acidified solution is extracted three times with ethyl acetate and the organic extracts combined, washed twice with sodium chloride solution and dried over sodium sulfate. The solvent is removed in vacuo and trituration with pet ether affords N-(1-methylcyclobutyl-oxycarbonyl)-phenylalanine, which is isolated by filtration.

When in the above procedure glycine methyl ester hydrochloride, alanine methyl ester hydrochloride, valine methyl ester hydrochloride, leucine methyl ester hydrochloride, isoleucine methyl ester hydrochloride, methionine methyl ester hydrochloride, proline methyl ester hydrochloride, tyrosine methyl ester hydrochloride, and serine methyl ester hydrochloride are used in place of phenylalanine methyl ester hydrochloride, there are obtained N-(1-methylcyclobutyloxycarbonyl)-glycine, N-(1-methylcyclobutyloxycarbonyl) alanine, N-(1-methylcyclobutyloxycarbonyl) valine, N-(1-methylcyclobutyloxycarbonyl) leucine, and N-(1-methylcyclobutyloxycarbonyl) isoleucine, N-(1-methylcyclobutyloxycarbonyl) methionine, N-(1-methylcyclobutyloxycarbonyl) proline, N-(1-methylcyclobutyloxycarbonyl) tyrosine, and N-(1-methylcyclobutyloxycarbonyl) serine respectively.

EXAMPLE 2

N-(1-Methylcyclobutyloxycarbonyl)-Phenylalanine-Alanine Methyl Ester

To a solution of 142 mg. (0.52 mM) of N-(1-methylcyclobutyloxycarbonyl) phenylalanine in 4 ml. acetonitrile is added 83 mg. (0.60 mM) alanine methyl ester hydrochloride and 80 microliters of triethylamine. Immediately following addition of the triethylamine, a solution of 119 mg. (0.58 mM) of N,N'-dicyclohexylcarbodiimide in 2 ml. of acetonitrile is added and the reaction is allowed to stir overnight at 20°–25°C. Excess N,N'-dicyclohexylcarbodiimide is destroyed by addition of 5 drops of 50% acetic acid. After adding 15 ml. of methylene chloride, the reaction mixture is filtered to remove the dicyclohexylurea formed during the reaction, and the filtrate is treated in the following manner: wash with saturated sodium bicarbonate, 50% saturated sodium chloride solution, 0.2 N sulfuric acid saturated with sodium sulfate, twice with 50% saturated sodium chloride solution. Repeat washing cycle with two portions of methylene chloride and dry over sodium sulfate. The solvent is removed and an oil is obtained. The oil is taken up in ethyl acetate, refluxed, and hexane is added until the cloud point. A solid is obtained when the reacton mixture is cooled to room temperature. Recrystallization from hot ethyl acetate-hexane affords 130 mg. of N-(1-methylcyclobutyloxycarbonyl) phenylalanine-alanine methyl ester.

EXAMPLE 3

N-(1-Methylcyclobutyloxycarbonyl)-Phenylalanine-Alanine Methyl Ester

A. Preparation of Hydroxysuccinimide Ester of N-(1-methylcyclobutyloxycarbonyl) Phenylalanine A sample of 2.02 mM of N-(1-methylcyclobutyloxycarbonyl) phenylalanine and 2.01 mM of N-hydroxysuccinimide are dissolved in 3.0 ml. of dry peroxide-free tetrahydrofuran at 0°–5°C. This solution is treated with 2.1 mM of N,N'-dicyclohexylcarbodiimide and allowed to react at 2°–5°C. Upon completion, the reaction is filtered to remove N,N'-dicyclohexylurea and the solvent removed in vacuo to afford the hydroxysuccinimide ester of N-(1-methylcyclobutyloxycarbonyl) phenylalanine.

When in the above procedure 1-hydroxypiperidine and p-nitrophenol are used in place of N-hydroxysuccinimide, there are obtained N-(1-methylcyclobutyloxycarbonyl) phenylalanine-1-piperidyl ester and N-(1-methylcyclobutyloxycarbonyl)-phenylalanine-p-nitrophenyl ester, respectively.

B. N-(1-Methylcyclobutyloxycarbonyl) Phenylalanine-Alanine Methyl Ester

A solution of 0.67 mM of the hydroxysuccinimide ester of N-(1-methylcyclobutyloxycarbonyl) phenylalanine and 0.70 mM of alanine methyl ester hydrochloride in 10 ml. of methylene chloride is treated with triethylamine until the pH is adjusted to 7.6–8.0. Reaction is stirred 6 hours and the reaction mixture is washed according to the following procedure: one time with dilute sodium bicarbonate solution; once with 50% saturated sodium chloride solution; once with 0.2 N sulfuric acid saturated with sodium sulfate; and two times with 50% saturated sodium chloride solution. The resulting material is dried over sodium sulfate and the washing procedure repeated. The solvent is removed in vacuo to afford N-(1-methylcyclobutyloxycarbonyl) phenylalanine-alanine methyl ester.

EXAMPLE 4

N-(1-Methylcyclohexyloxycarbonyl)-Phenylalanine

A. Preparation of 1-Methylcyclohexyl Chloroformate

A solution of 40 mM of phosgene in 20 ml. of benzene is prepared by bubbling the phosgene into the solvent at 0°C. A mixture of 2.5 ml. (20 mM) of 1-methylcyclohexanol and 1.70 ml. (20 mM) of pyridine in 20 ml. of benzene is added slowly over 20 minutes at 0°C. The reaction is allowed to stir for 2½ hours at 0°C. The excess phosgene is removed by evacuation under aspirator pressure and the benzene mixture filtered to remove pyridine hydrochloride. The filtrate is concentrated in vacuo to a volume of 5–6 ml. containing 1-methylcyclohexyl chloroformate. The solution is kept at 0°C. and employed in the following reaction.

B. N-(1-Methylcyclohexyloxycarbonyl)-Phenylalanine

A suspension of 0.59 g. (2.1 mM) of phenylalanine methylester hydrochloride in 10 ml. of chloroform is cooled to 0°C. After the pH of the mixture is adjusted to 8 by addition of triethylamine, 4.5 mM of 1-methylcyclohexyl chloroformate is added portion-wise at 0°C. while maintaining the pH of the reaction at 8 by addition of triethylamine. The reaction is stirred overnight at 20°–25°C. After adding chloroform, the reaction mixture is washed with 5% sodium bicarbonate solution, 50% saturated sodium chloride solution, 0.2 N sulfuric acid saturated with sodium sulfate, twice with 50% saturated sodium chloride solution, and then the reaction solution is dried over sodium sulfate. The solvent is removed to afford an oil of 1-methylcyclohexyloxycarbonyl phenylalanine methyl ester.

Saponification of the above ester is accomplished by dissolving the oil in 10 ml. of methanol; 10 ml. of water is added and the pH of the mixture adjusted to 12 by addition of 1 N sodium hydroxide. The reaction is allowed to stir for 46 hours at 25°C. The pH of the reaction is adjusted to 7 by addition of 2 N sulfuric acid. The methanol solvent is removed in vacuo, saturated sodium bicarbonate is added to the residual aqueous solution, and then washed twice with ether. The reaction mixture is acidified by dropwise addition of concentrated sulfuric acid to pH 3.0, extracted three times with ethyl acetate, wash the combined organic layers twice with sodium chloride solution and dry over sodium sulfate. After removing the solvent in vacuo, 758 mg. of substantially pure N-(1-methylcyclohexyloxycarbonyl)-phenylalanine is obtained.

When in the above procedure glycine methyl ester hydrochloride, alanine methyl ester hydrochloride, valine methyl ester hydrochloride, leucine methyl ester hydrochloride, isoleucine methyl ester hydrochloride, methionine methyl ester hydrochloride, proline methyl ester hydrochloride, tyrosine methyl ester hydrochloride, and serine methyl ester hydrochloride are used in place of phenylalanine methyl ester hydrochloride, there are obtained N-(1-methylcyclohexyloxycarbonyl) glycine, N-(1-methylcyclohexyloxycarbonyl)-valine, N-(1-methylcyclohexyloxycarbonyl)-leucine, N-(1-methylcyclohexyloxycarbonyl)-isoleucine, N-(1-methylcyclohexyloxycarbonyl-methionine, N-(1-methylcyclohexyloxycarbonyl)-proline, N-(1-methyl-cyclohexyloxycarbonyl)-tyrosine, and N-(1-methylcyclohexyloxycarbonyl)-serine, respectively.

EXAMPLE 5

N-(1-Methylcyclohexyloxycarbonyl)-Phenylalanine-Alanine Methyl Ester

To a solution of 0.52 mM of N-(1-methylcyclohexyloxycarbonyl) phenylalanine in 4 ml. acetonitrile is added 0.60 mM alanine methyl ester hydrochloride and 80 microliters of triethylamine. Immediately following addition of the triethylamine, a solution of 0.58 mM of N,N'-dicyclohexylcarbodiimide in 2 ml. of acetonitrile is added and the reaction is allowed to stir overnight at 20°–25°C. Excess N,N'-dicyclohexylcarbodiimide is destroyed by addition of 5 drops of 50% acetic acid. After adding 15 ml. of methylenechloride, the reaction mixture is filtered to remove the dicyclohexylurea formed during the reaction and the filtrate is treated in the following manner: wash with saturated sodium bicarbonate, 50% saturated sodium chloride solution, 0.2 N sulfuric acid saturated with sodium sulfate, twice with 50% saturated sodium chloride solution. Repeat washing cycle with two portions of methylene chloride and dry over sodium sulfate. The solvent is removed and substantially pure N-(1-methylcyclohexyloxycarbonyl) phenylalanine-alanine methyl ester is obtained.

EXAMPLE 6

N-(1-Methylcyclohexyloxycarbonyl)-Phenylalanine-Alanine Methyl Ester

A. Preparation of Hydroxysuccinimide Ester of N-(1-methylcyclohexyloxycarbonyl) Phenylalanine A sample of 2.02 mM of N-(1-methylcyclohexyloxycarbonyl) phenylalanine and 2.01 mM of N-hydroxysuccinimide are dissolved in 3.0 ml. of dry peroxide-free tetrahydrofuran at 0°–5°C. This solution is treated with 2.1 mM of N,N'-dicyclohexylcarbodiimide and allowed to react at 2°–5°C. Upon completion, the reaction is filtered to remove N,N'-dicyclohexylurea and the solvent removed in vacuo to afford the hydroxysuccinimide ester of N-(1-methylcyclohexyloxycarbonyl) phenylalanine.

When in the above procedure 1-hydroxypiperidine and p-nitrophenol are used in place of N-hydroxysuccinimide, there are obtained N-(1-methylcyclohexyloxycarbonyl) phenylalanine-1-piperidyl ester and N-(1-methylcyclohexyloxycarbonyl)-phenylalanine-p-nitrophenyl ester, respectively.

B. N-(1-Methylcyclohexyloxycarbonyl) Phenylalanine-Alanine Methyl Ester

A solution of 0.67 mM of the hydroxysuccinimide ester of N-(1-methylcyclohexyloxycarbonyl) phenylalanine and 0.70 mM of alanine methyl ester hydrochloride in 10 ml. of methylene chloride is treated with triethylamine until the pH is adjusted to 7.6–8.0. Reaction is stirred six hours and the reaction mixture is washed according to the following procedure: one time with dilute sodium bicarbonate solution; once with 50% saturated sodium chloride solution; once with 0.2 N sulfuric acid saturated with sodium sulfate; and two times with 50% saturated sodium chloride solution. The resulting material is dried over sodium sulfate and the washing procedure repeated. The solvent is removed in vacuo to afford N-(1-methylcyclohexyloxycarbonyl) phenylalanine-alanine methyl ester.

EXAMPLE 7

Aspartyl-Phenylalanine Methyl Ester

A. Preparation of N-(1-Methylcyclobutyloxycarbonyl) Aspartic Acid

A suspension of 0.05 moles of aspartic acid dimethyl ester hydrochloride in 50 ml. of chloroform is cooled to 0°C. and the pH adjusted to 8 by addition of triethylamine. 1-Methylcyclobutyl chloroformate 0.10 moles prepared according to the procedure of Example 1 is added portion-wise at 0°C. and the pH of the reaction is maintained at 8 by addition of triethylamine. Upon completion of the addition, the reaction is stirred overnight at 20°–25°C. The reaction solution is washed successively with 10 ml. portions of a saturated sodium bicarbonate solution, 50% saturated solution of sodium chloride, 0.2 N sulfuric acid saturated with sodium sulfate, 50% saturated solution of sodium chloride (twice), and the chloroform solution is dried over sodium acetate. Removal of the chloroform affords N-(1-methylcyclobutyloxycarbonyl)-aspartic acid dimethyl ester. Saponification is accomplished by dissolving the ester in 50 ml. of methanol, water 50 ml. is added, and the pH is adjusted to 12 by addition of 2 N sodium hydroxide. After stirring overnight at 25°C., the pH is adjusted to 7 with 2N sulfuric acid. The methanol is removed in vacuo and saturated sodium bicarbonate solution is added to the water solution. The aqueous bicarbonate solution is washed two times with ether and then the pH is adjusted to 3 by addition of concentrated hydrochloric acid. The acidified solution is extracted three times with ethyl acetate and the organic extracts combined, washed twice with sodium chloride solution and dried over sodium sulfate. The solvent is removed in vacuo to afford N-(1-methylcyclobutyloxycarbonyl) aspartic acid.

B. Preparation of N-(1-Methylcyclobutyloxycarbonyl)-Aspartic Anhydride

A solution of 2.45 g. of N-(1-methylcyclobutyloxycarbonyl)-aspartic acid in 50 ml. of dioxane is prepared and 2.2 g. of dicyclohexylcarbodiimide is added with vigorous stirring. After stirring at 25°C. for 2 hours, the dicyclohexylurea is removed by filtration and the dioxane removed by evaporation in vacuo. The resulting solid is substantially pure N-(1-methylcyclobutyloxycarbonyl)-aspartic anhydride.

C. Preparation of N-(1-Methylcyclobutyloxycarbonyl)-Aspartyl Phenylalanine Methyl Ester About 2.27 g. of N-(1-methylcyclobutyloxycarbonyl)-aspartic anhydride, 2.15 g. of phenylalanine methyl ester hydrochloride, and 0.95 g. of triethylamine are dissolved in about 50 ml. of dimethylformamide and the resulting solution stirred at 20°C. for 4 hours. The solution is evaporated to dryness and dissolved in about 150 ml. of ethyl acetate. The ethyl acetate solution is extracted with 2 × 150 ml. of 1 N sulfuric acid, dried over sodium sulfate, and evaporated to dryness in vacuo to give a mixture of α and β N-(1-methylcyclobutyloxycarbonyl)-aspartyl-phenylalanine methyl ester.

D. Aspartyl-Phenylalanine Methyl Ester

A mixture of α and β N-(1-methylcyclobutyloxycarbonyl) aspartyl-phenylalanine methyl ester (1 g.) is dissolved in 16 ml. of anhydrous hydrofluoric acid at 0°C. with stirring. After stirring for 45 minutes at 0°C., the solution is evaporated to dryness under a stream of nitrogen. The resulting solid mixture of α and β aspartyl phenylalanine methyl ester is dissolved in water and the pH adjusted to 3–5 with sodium hydroxide. The α-isomer is precipitated by the addition of an organic acid such as β-phenyl propionic acid and isolated by filtration. When in Step A of the above procedure 1-methylcyclohexyl chloroformate is used in place of 1-methylcyclobutyl chloroformate, N-(1-methylcyclohexyloxycarbonyl)-aspartic acid is obtained. The compound is converted to aspartyl-phenylalanine methyl ester according to the procedures of Steps B, C, and D above.

Various changes and modifications in the procedures herein disclosed will occur to those skilled in the art, and to the extent that such changes and modifications are embraced by the appended claims, it is to be understood that they constitute part of our invention. What is claimed is:

1. A compound of the formula:

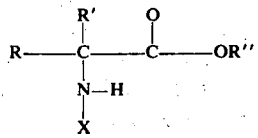

wherein X is selected from the group consisting of 1-methylcyclobutyloxycarbonyl and 1-methylcyclohexyloxycarbonyl; R' is hydrogen; R is hydrogen, loweralkyl, or substituted loweralkyl wherein the substituent is selected from the group consisting of hydroxy, amino, carboxy, benzyl and hydroxybenzyl; and R" is hydrogen, benzyl or loweralkyl.

2. The compound of claim 1 wherein X is 1-methylcyclobutyloxycarbonyl.
3. The compound of claim 2 wherein R" is hydrogen.
4. The compound of claim 2 wherein R" is loweralkyl.
5. The compound of claim 4 wherein R" is methyl.
6. The compound of claim 1 wherein X is 1-methylcyclohexyloxycarbonyl.
7. The compound of claim 6 wherein R" is hydrogen.
8. The compound of claim 6 wherein R" is loweralkyl.
9. The compound of claim 8 wherein R" is methyl.
10. The compound N-(1-methylcyclobutyloxycarbonyl) phenylalanine.
11. The compound N-(1-methylcyclohexyloxycarbonyl) phenylalanine.
12. The compound of claim 1 wherein R is hydrogen.

* * * * *